(12) United States Patent
Towler

(10) Patent No.: US 11,358,109 B2
(45) Date of Patent: Jun. 14, 2022

(54) STORAGE, MIXING AND DISPENSING DEVICE

(71) Applicant: Mark Robert Towler, Toronto (CA)

(72) Inventor: Mark Robert Towler, Toronto (CA)

( * ) Notice: Subject to any disclaimer, the term of this patent is extended or adjusted under 35 U.S.C. 154(b) by 316 days.

(21) Appl. No.: 16/636,369

(22) PCT Filed: Aug. 2, 2018

(86) PCT No.: PCT/CA2018/050948
§ 371 (c)(1),
(2) Date: Feb. 4, 2020

(87) PCT Pub. No.: WO2019/023805
PCT Pub. Date: Feb. 7, 2019

(65) Prior Publication Data
US 2020/0164324 A1 May 28, 2020

Related U.S. Application Data

(60) Provisional application No. 62/541,227, filed on Aug. 4, 2017.

(51) Int. Cl.
*B01F 35/71* (2022.01)
*B01F 25/451* (2022.01)
(Continued)

(52) U.S. Cl.
CPC ...... *B01F 35/7174* (2022.01); *A61B 17/8825* (2013.01); *A61L 24/06* (2013.01);
(Continued)

(58) Field of Classification Search
CPC .......... B01F 35/7174; B01F 35/717; B01F 25/4512; B01F 25/451; B01F 25/45; B01F 25/4521; B01F 31/40; B01F 33/50112; B01F 33/5011; B01F 35/514; B01F 35/50; B01F 35/754251; B01F 21/00; B01F 2101/20; A61B 17/8825; A61B 17/8802;
(Continued)

(56) References Cited

U.S. PATENT DOCUMENTS

| 4,676,406 A | 6/1987 | Frischmann et al. |
| 5,193,907 A | 3/1993 | Faccioli et al. |

(Continued)

FOREIGN PATENT DOCUMENTS

| CA | 3070608 A1 | 2/2019 |
| EP | 2764841 B1 | 8/2014 |

OTHER PUBLICATIONS

International Search Report and Written Opinion dated Oct. 16, 2018 in corresponding International Patent Application No. PCT/CA2018/050948 (15 pages).
(Continued)

*Primary Examiner* — David J Walczak
(74) *Attorney, Agent, or Firm* — Bereskin & Parr LLP/S.E.N.C.R.L., s.r.l.; Tony Orsi

(57) ABSTRACT

Various embodiments are described herein for a device for storing first and second ingredient materials, mixing the ingredient materials to form an adhesive material and dispensing the adhesive material. Various embodiments are also described herein for a method of making the device and a method of using the device.

28 Claims, 7 Drawing Sheets

(51) Int. Cl.
*B01F 25/452* (2022.01)
*B01F 31/40* (2022.01)
*B01F 33/501* (2022.01)
*B01F 35/50* (2022.01)
*B01F 35/75* (2022.01)
*B01F 21/00* (2022.01)
*A61B 17/88* (2006.01)
*A61L 24/06* (2006.01)
*A61L 24/12* (2006.01)
*B05C 17/005* (2006.01)
*C08K 3/40* (2006.01)
*B01F 101/20* (2022.01)

(52) U.S. Cl.
CPC .............. *A61L 24/12* (2013.01); *B01F 21/00* (2022.01); *B01F 25/4512* (2022.01); *B01F 25/4521* (2022.01); *B01F 31/40* (2022.01); *B01F 33/50112* (2022.01); *B01F 35/514* (2022.01); *B01F 35/754251* (2022.01); *B05C 17/00563* (2013.01); *B05C 17/00566* (2013.01); *B05C 17/00593* (2013.01); *C08K 3/40* (2013.01); *A61B 2017/8838* (2013.01); *A61L 2430/02* (2013.01); *B01F 2101/20* (2022.01)

(58) Field of Classification Search
CPC . A61B 2017/8838; A61L 24/06; A61L 24/12; A61L 2430/02; B05C 17/00563; B05C 17/00559; B05C 17/00553; B05C 17/00566; B05C 17/593; C08K 3/40
USPC .... 401/40–42, 176, 178, 179; 366/244, 241, 366/247, 130, 189, 277; 206/219, 221; 222/129, 137, 134, 140, 386
See application file for complete search history.

(56) References Cited

U.S. PATENT DOCUMENTS

| | | | |
|---|---|---|---|
| 5,842,785 A | 12/1998 | Brown et al. | |
| 6,017,349 A | 1/2000 | Heller et al. | |
| 6,033,105 A | 3/2000 | Barker et al. | |
| 6,406,175 B1 | 6/2002 | Marino | |
| 6,655,828 B2 * | 12/2003 | Vendrely | B01F 33/5011 366/169.2 |
| 7,168,847 B2 | 1/2007 | Frei et al. | |
| 7,216,761 B2 | 5/2007 | De Vries | |
| 7,393,342 B2 | 7/2008 | Henniges et al. | |
| 7,441,943 B2 | 10/2008 | Barker et al. | |
| 7,524,103 B2 | 4/2009 | McGill et al. | |
| 7,938,572 B2 | 5/2011 | Lidgren et al. | |
| 8,256,646 B2 | 9/2012 | Keller | |
| 9,060,826 B2 * | 6/2015 | Coale | A61B 17/8822 |
| 9,061,257 B2 | 6/2015 | Greter et al. | |
| 9,095,871 B2 | 8/2015 | Vogt et al. | |
| 9,132,573 B2 * | 9/2015 | Vogt | B01F 35/7131 |
| 9,339,946 B2 | 5/2016 | Vogt et al. | |
| 9,358,715 B2 | 6/2016 | Quinto | |
| 9,456,861 B2 | 10/2016 | Anderson et al. | |
| 9,480,955 B2 | 11/2016 | Sasaki et al. | |
| 2003/0012080 A1 | 1/2003 | Coffeen et al. | |
| 2004/0122359 A1 | 6/2004 | Wenz et al. | |
| 2005/0111300 A1 | 5/2005 | Nies et al. | |
| 2005/0128868 A1 | 6/2005 | Vries | |
| 2006/0164913 A1 | 7/2006 | Arramon | |
| 2006/0274601 A1 | 12/2006 | Seaton | |
| 2009/0314803 A1 | 12/2009 | Keller | |
| 2010/0114067 A1 | 5/2010 | Trieu et al. | |
| 2012/0155214 A1 | 6/2012 | Faccioli et al. | |
| 2014/0135780 A1 | 5/2014 | Lee et al. | |
| 2014/0269147 A1 | 9/2014 | Click et al. | |
| 2015/0009775 A1 | 1/2015 | Vogt | |
| 2015/0164568 A1 | 6/2015 | Vogt | |
| 2015/0216577 A1 | 8/2015 | Vogt et al. | |

OTHER PUBLICATIONS

Extended European Search Report dated Apr. 19, 2021 in EP Patent Application No. 18841504.6 (7 pages).

* cited by examiner

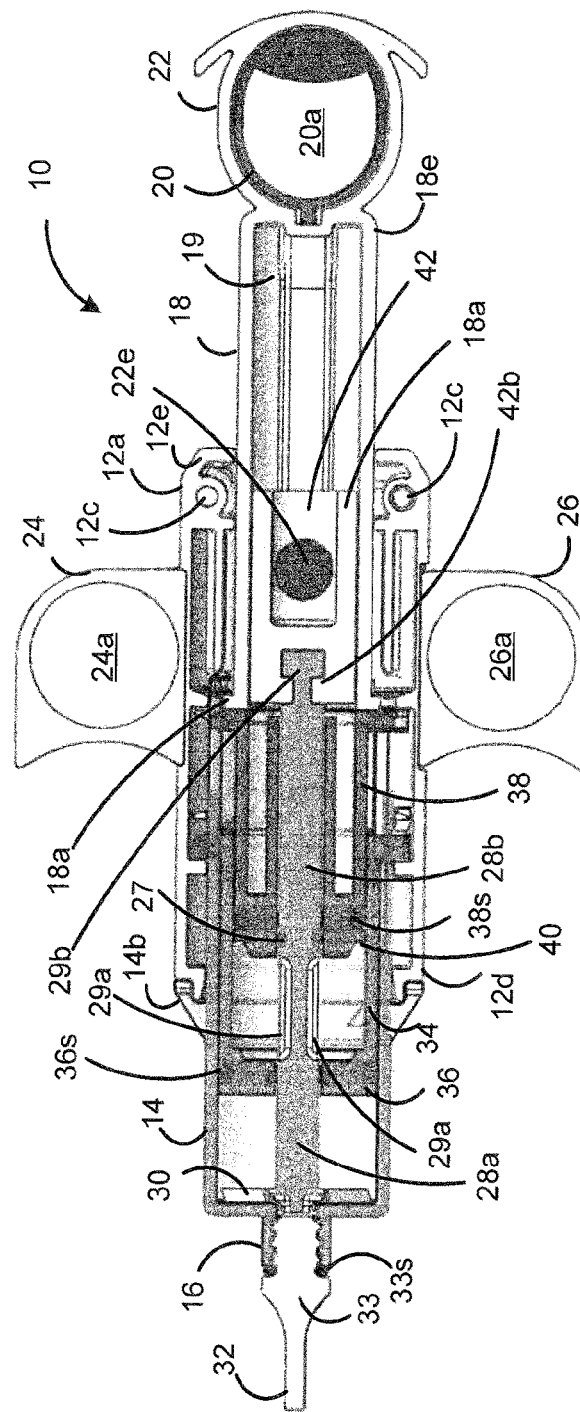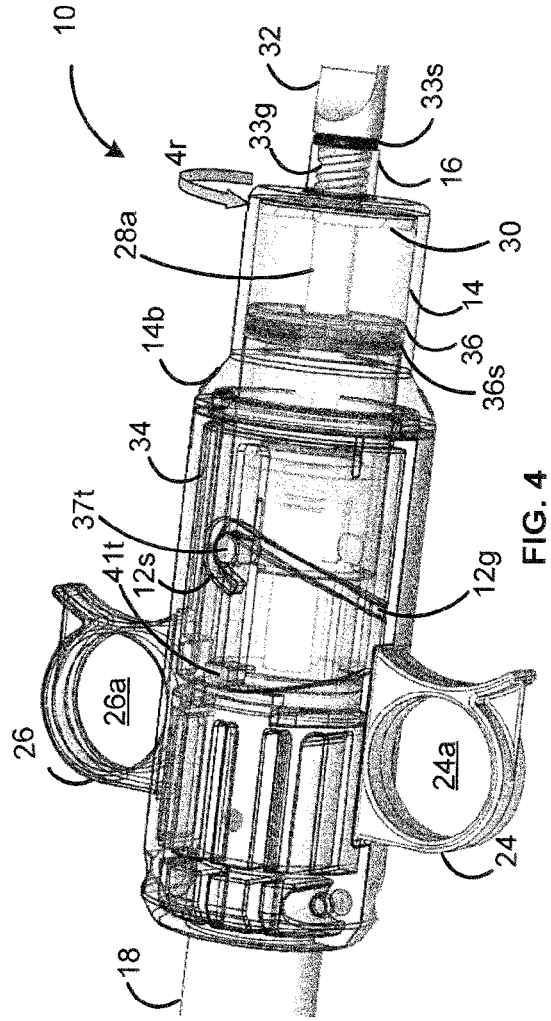
FIG. 3
FIG. 4

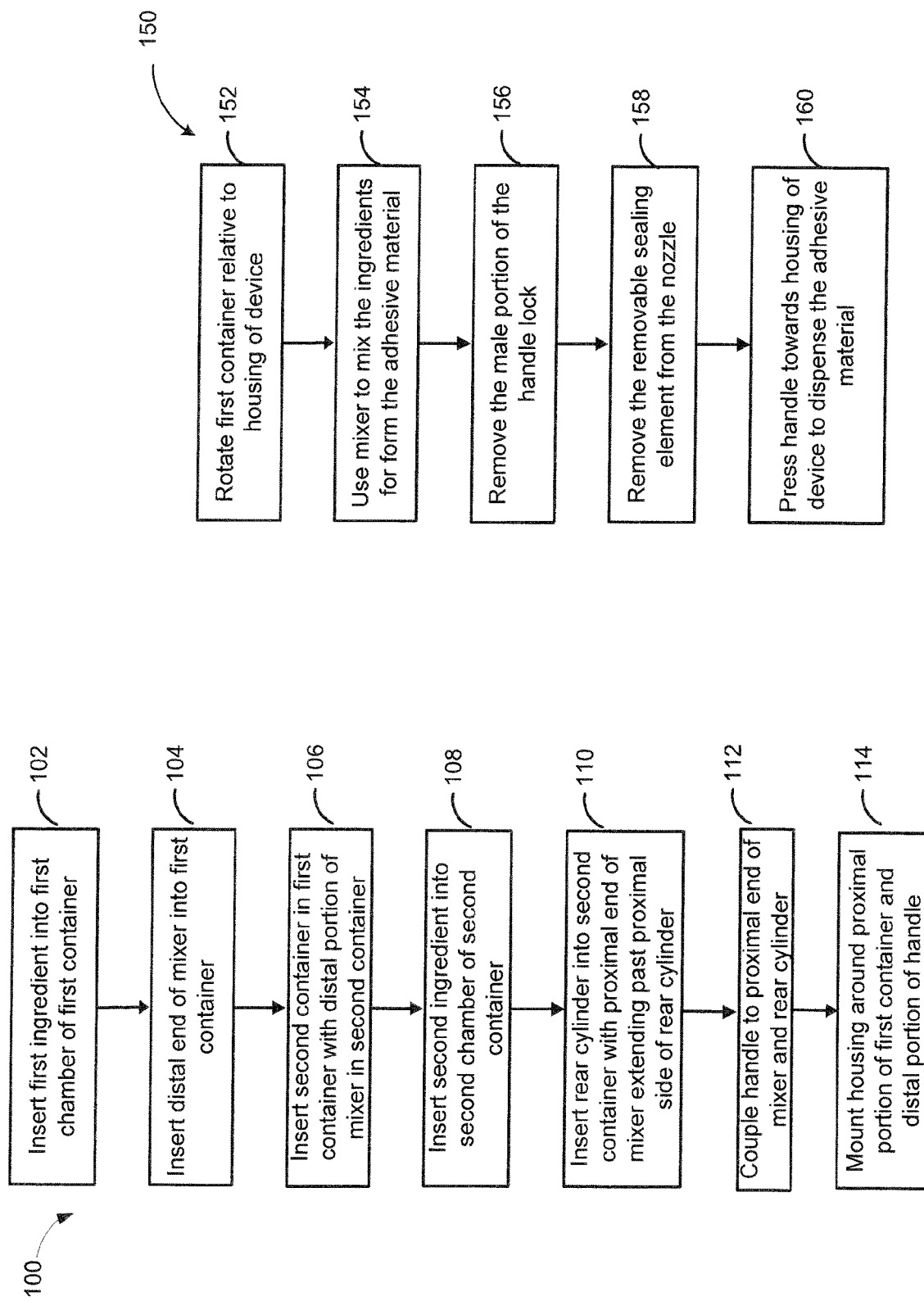

STORAGE, MIXING AND DISPENSING DEVICE

This application is a 35 USC 371 national stage entry of International Patent Application No. PCT/CA2018/050948, filed Aug. 2, 2018, which claims the benefit of U.S. Provisional Patent Application No. 62/541,227, filed Aug. 4, 2017, and entitled "A STORAGE, MIXING AND DISPENSING DEVICE"; the entire contents of each of which are hereby incorporated by reference.

CROSS-REFERENCE

This application claims the benefit of U.S. Provisional Patent Application No. 62/541,227, filed Aug. 4, 2017, and the entire content of U.S. Provisional Patent Application No. 62/541,227 is hereby incorporated by reference.

FIELD

Various embodiments are described herein for an apparatus and method that may be used for storing and mixing two materials and then injecting the mixed materials and in particular for performing mixing and injecting for various purposes including medical and dental purposes.

BACKGROUND

In certain applications it is necessary to combine ingredient materials to form an adhesive material which is then used to perform a particular action. Since the action may not be performed right away and since the ingredient materials may react with one another when they make contact, the ingredient materials are stored in separate areas and then combined, or mixed, to form the adhesive material at a later time when the adhesive material is needed for use.

SUMMARY OF VARIOUS EMBODIMENTS

Various embodiments of methods and devices for storing ingredient materials, mixing the ingredient materials to form an adhesive material and dispensing the adhesive material are provided according to the teachings herein.

In a broad aspect, at least one embodiment described herein provides a device for storing ingredient materials, mixing the ingredient materials to form a third material and dispensing the third material, wherein the device comprises a nozzle at a first end of the device for dispensing the third material from the device after mixing; a first container at a distal end of the device and coupled with the nozzle, the first container being adapted to store a first ingredient material and mix the first ingredient material with a second ingredient material to create the third material; a second container that is disposed within a distal portion of the first container, has an aperture in communication with the first container and is moveable within the device between a storage position in which a second ingredient material is stored in the second container and a mixing position in which the second ingredient material is moved to the first container; a mixer that longitudinally extends into the first and second containers and is used to mix the first and second ingredient materials; a handle at a proximal end of the device, the handle being coupled to the mixer to mix the first and second ingredient materials and the handle also being coupled to the second container to move the second container to a dispensing position to dispense the third material; and a removable sealing element disposed at the nozzle when storing and mixing the first and second ingredient materials and being removed when dispensing the third material from the device.

In at least some embodiments, the device further comprises a removable handle lock that is disposed at the handle, wherein when the handle lock is in place movement of the handle is allowed along a mixing pathway to move the mixer and when the handle lock is removed movement of the handle is allowed along a dispensing pathway to move the second container to the dispensing position in which the second container is moved further into the first container for dispensing the third material.

In at least some embodiments, the first and second containers are made of transparent material allowing for visual inspection of the first and second ingredient materials during storage and mixing.

In at least some embodiments, the device comprises a housing disposed at a mid-portion of the device with a portion of the first container extending past a distal end of the housing, a portion of the handle extending past a proximal end of the housing and both the first container and the second container being rotatable with respect to the housing for mixing the first and second ingredient materials.

In at least some embodiments, the first container comprises sidewalls with at least one guide channel along a portion of the sidewalls; the housing comprises at least one inclined groove on an inner surface thereof; and the second container comprises at least one protrusion on an outer surface thereof that is received within the at least one guide channel and radially extends past the sidewalls of the first container and extends into and engages the at least one inclined groove of the housing, wherein during use the first container is twisted relative to the housing thereby causing the at least one protrusion of the second container to move along the at least one inclined groove of the housing and move the second container away from the distal end of the first container to move the second ingredient material from the second container to the first container.

In at least some embodiments, the mixer comprises at least one mixing groove on an outer surface thereof wherein during mixing a first portion of the at least one mixing groove is disposed within the first container and a second portion of the at least one mixing groove is disposed within the second container to allow the second ingredient material to move from the second container to the first container during mixing.

In at least some embodiments, the mixer comprises a mixing element at an end portion thereof which is disposed within the first container for mixing the first and second ingredient materials.

In at least some embodiments, the mixing element is rotatable and longitudinally translatable for mixing the first and second ingredient materials.

In at least some embodiments, the first container comprises a first cylinder having: the nozzle at a first end of the cylinder; a first chamber formed by sidewalls of a distal portion of the first cylinder, the first chamber acting as a storage chamber and as a mixing chamber and being in communication with the nozzle; and a first guide region formed by sidewalls of a proximal portion of the first cylinder and the at least one guide channel is located in the first guide region.

In at least some embodiments, the second container comprises a second cylinder moveable with respect to the first cylinder and having a diameter smaller than a diameter of the first cylinder, the second cylinder having: a first end having an aperture in communication with the first cylinder; a second chamber formed by sidewalls of a distal portion of the second cylinder, the second chamber acting as a second storage chamber for the second ingredient material; a first sealing member disposed around a portion of the distal sidewalls of the second chamber for providing sealing for the first chamber; and a second guide region formed by sidewalls of a proximal portion of the second cylinder and the at least one protrusion is located on an outer surface of the second guide region, wherein the second container is received within the first guide region.

In at least some embodiments, the device further comprises a rear cylinder moveable with respect to the second cylinder and having a diameter smaller than a diameter of the second cylinder, the rear cylinder comprising: an aperture at a distal end; an axial channel aligned with the aperture, the mixer extending along the axial channel through the aperture; at least one protrusion on an exterior surface of the rear cylinder for sliding within the at least one guide channel of the first cylinder during use; a flat surface at a proximal end of the rear cylinder for receiving a distal portion of the handle when the handle lock is removed thereby moving the rear cylinder towards the first and second cylinders; and a second sealing member disposed around the distal sidewalls of the rear cylinder for providing sealing for the second chamber.

In at least some embodiments, the housing comprises first and second finger grips disposed on opposite sides of an exterior surface of the housing and the handle comprises a third finger grip at a proximal end thereby allowing a user to hold the device and move the handle towards the housing during mixing and/or dispensing.

In at least some embodiments, the finger grips are rings.

In at least some embodiments, the handle comprises a groove on an exterior surface thereof, an aperture at one end of the groove and an interior axial channel at a distal end thereof coupled with the aperture; and the handle lock comprises: a female locking member that is sized to be received within the interior axial channel of the handle and has an aperture at a proximal end that aligns with the aperture of the handle and a distal end with an engagement member that is coupled with the mixer; and a male locking member removably disposed within the groove on the handle and having a post at a distal end thereof for engaging the apertures of the handle and the female locking member to constrain the movement of the handle along the mixing pathway.

In at least some embodiments, the male locking member comprises a handle at a proximal end thereof for removing the male locking member from the groove on the handle.

In at least some embodiments, the handle of the male locking member is a finger grip ring that is disposed within the finger grip of the handle.

In at least some embodiments, the male locking member is removed the female locking member is free to move within the handle allowing the handle to move along the dispensing pathway where a distal portion of the handle pushes the second container further into the first container to dispense the third material from the device.

In another broad aspect, at least one embodiment described herein provides a device for storing first and second ingredient materials, mixing the ingredient materials to form an third material and dispensing the third material, wherein the device comprises: a nozzle and having a removable sealing element; a housing; a first container rotatably coupled to the housing, being in fluid communication with the nozzle, and having a first chamber for storing the first ingredient material during storage; a second container disposed in the first container and in the housing, having a second chamber for storing the second ingredient material during storage and an aperture that is in fluid communication with the first container, the second container being linearly moveable with respect to the first container and rotatably coupled to the housing; a rear cylinder being disposed in the housing and in the first container proximal to the second container, the rear cylinder having a second aperture at a distal end, the rear cylinder being linearly moveable with respect to the first container and rotatably coupled to the housing; a mixer that longitudinally extends through the apertures of the second container and the rear cylinder into the first chamber for mixing the first and second ingredient materials during mixing; and a handle extending from a proximal end of the housing and having a handle lock, the handle being coupled to the mixer to control the mixer when the handle lock is in place and the handle being coupled to the rear cylinder to move the rear cylinder and the second container toward the nozzle to dispense the third material from the first container when the handle lock and the sealing element are removed, wherein, during use, when the first container is rotated the second container moves towards the rear cylinder, the second chamber reduces in size, the first chamber increases in size and the second material moves into the first chamber for mixing.

In another broad aspect, at least one embodiment described herein provides a method of making a device for storing first and second ingredient materials, mixing the ingredient materials to form an third material and dispensing the third material, wherein the method comprises: inserting the first ingredient material into a first chamber of a first container having a nozzle at a distal end and an open proximal end, the nozzle being sealed by a removable sealing member; inserting a mixer having a mixing element longitudinally through an aperture on a distal end of a second container having a second chamber and an open proximal end; inserting a distal end of the second container into the first container with the mixing element of the mixer extending into the first chamber, the first and second containers having a linear translational coupling; inserting the second ingredient material into the second chamber of the second container; inserting a rear cylinder having an axial channel into the second container with a proximal end of the mixer extending past a proximal end of the rear cylinder, the rear cylinder and the first container having a linear translational coupling; coupling a handle with a handle lock to the mixer; and mounting a housing around a proximal portion of the first container and a distal portion of the handle, the housing and the first container having a rotational coupling and the housing and the second container and the rear cylinder having a rotational and linearly translational coupling.

In another broad aspect, at least one embodiment described herein provides a method of using a device for mixing first and second ingredients to form an third material and dispensing the third material, the device being defined according to at least one of the embodiments described herein, wherein the method comprises: rotating the first container relative to the housing of the device; using the mixer to mix the first and second ingredients for forming the third material; removing the male locking member of the handle lock; removing the removable sealing element from the nozzle; and moving the handle towards the housing of the device to dispense the third material.

In at least one of the device and method embodiments, the third material is an adhesive material.

In at least one of the device and method embodiments, the first ingredient material stored in the first chamber is a powder and the second ingredient material stored in the second chamber is a liquid, wherein the powder comprises an ionomeric glass and the liquid comprises an aqueous polyacrylic acid.

In at least one of the device and method embodiments, the first ingredient material stored in the first chamber is a powder and the second ingredient material stored in the second chamber is a liquid, wherein the powder comprises an ionomeric glass and dehydrated polyacrylic acid and the liquid comprises water.

In at least one of the device and method embodiments, the first ingredient material stored in the first chamber is a powder and the second ingredient material stored in the second chamber is a liquid, wherein the powder comprises dehydrated acid and the liquid comprises water having dissolved ionomeric glass therein.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIG. 3 is a top cross-sectional view of the device of FIG. 1 in a storage configuration in which two materials are stored separately from one another.

FIG. 4 is a transparent view of a portion of the device of FIG. 1 showing how the materials are initially mixed.

FIG. 8A shows a flowchart of an example embodiment of a method for making a device that can be used to store, mix and dispense materials in accordance with the teachings herein.

FIG. 8B shows a flow chart of an example embodiment of a method for using the device of FIG. 1 to mix and dispense materials in accordance with the teachings herein.

Figure 1:
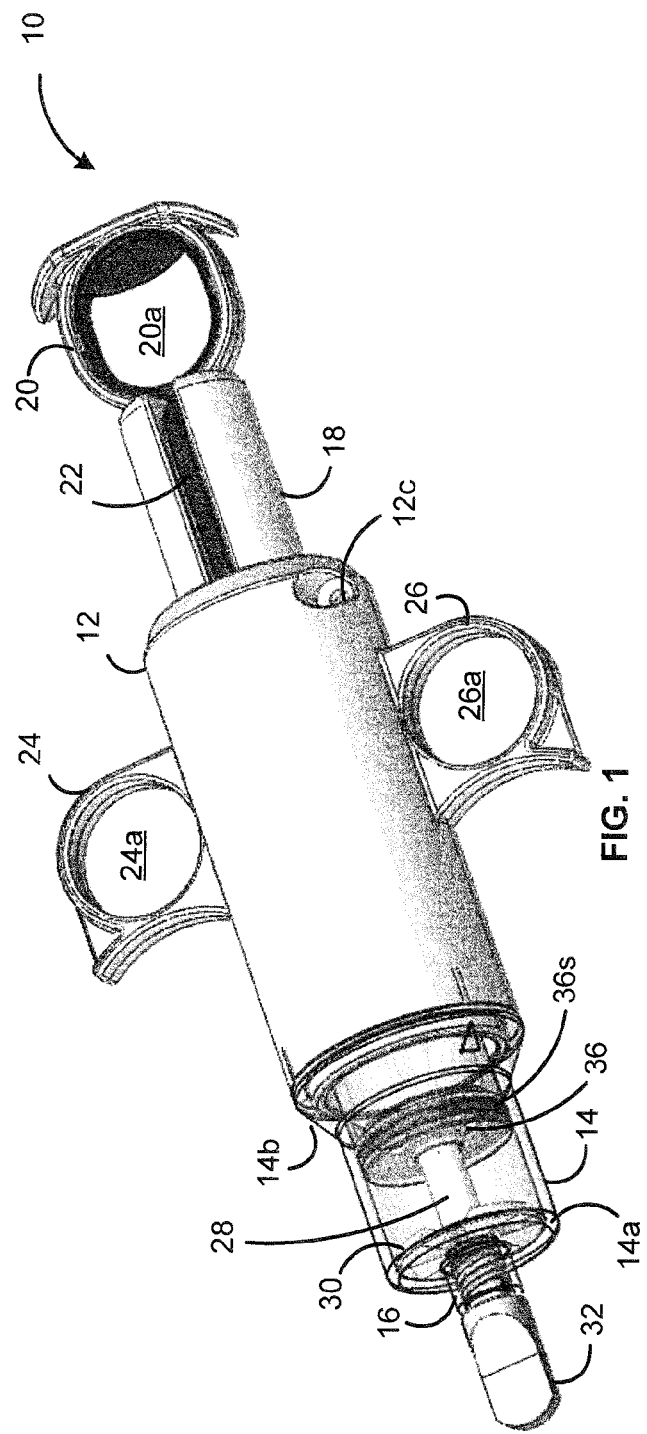
FIG. 1 is a perspective view of an example embodiment of a storing, mixing and injection device in accordance with the teachings herein.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices or methods having all of the features of any one of the devices or methods described below or to features common to multiple or all of the devices and or methods described herein. It is possible that there may be a device or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical electrical connotation. For example, as used herein, the terms coupled or coupling can indicate that two elements or devices can be directly connected to one another or connected to one another through one or more intermediate mechanical elements or devices, depending on the particular context.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "similarly", "about" and "approximately" as used herein mean a reasonable amount of deviation of the modified term such that the end result is not significantly changed. These terms of degree may also be construed as including a deviation of the modified term, such as 1%, 2%, 5%, or 10%, for example, if this deviation does not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as up to 1%, 2%, 5% or 10%, for example.

Figure 2:
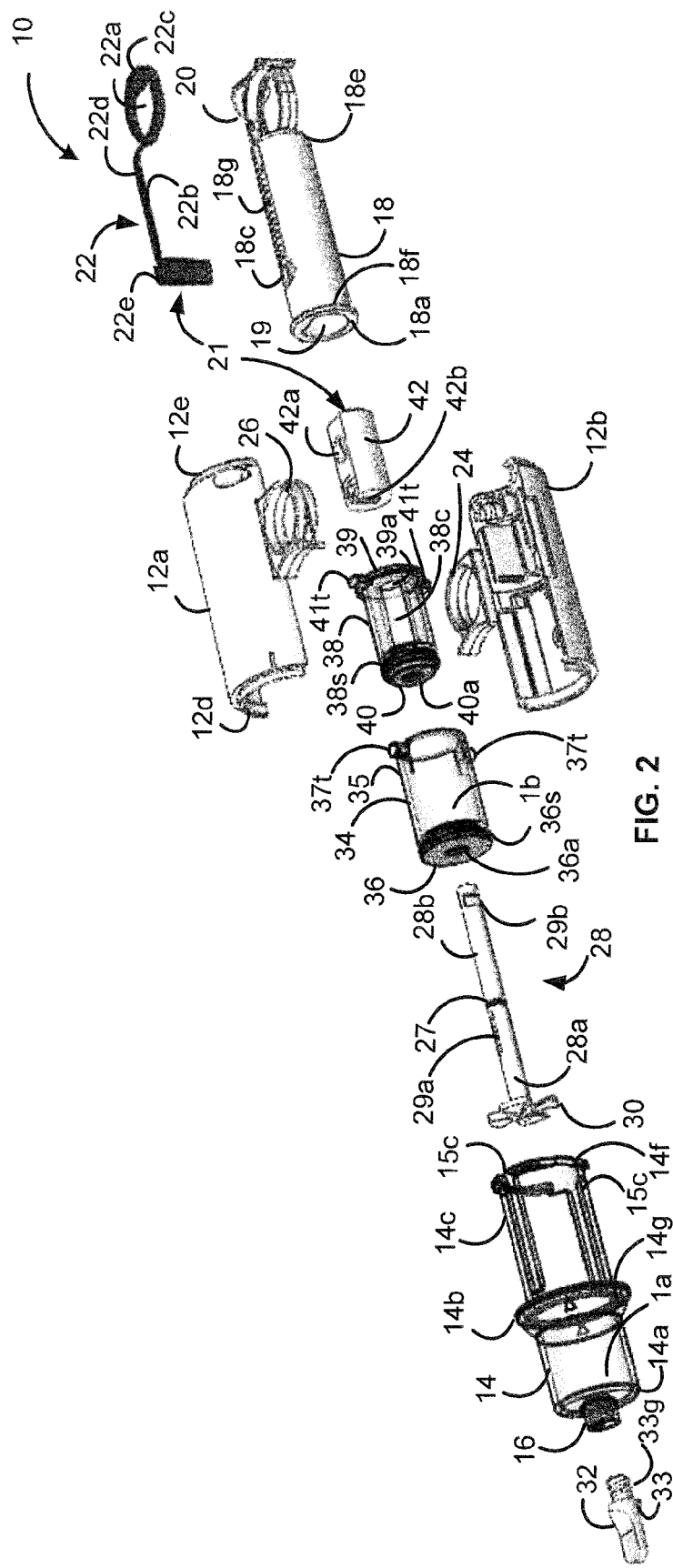
FIG. 2 is an exploded perspective view of the device of FIG. 1.

Referring now to FIGS. 1 to 3, illustrated therein is a perspective view of an example embodiment of a storing, mixing and injection device 10 in accordance with the teachings herein. The device 10 is implemented to be quick and easy to activate by an untrained user. The device 10 generally has three modes of operation including: 1) storage, 2) mixing and 3) dispensing. In the storage mode, first and second ingredient materials for making an adhesive material are stored separately from one another in first and second storage chambers, respectively. During the mixing mode, the second material from the second storage chamber is moved to the first storage chamber and the first storage chamber is used as a mixing chamber where the first and second ingredient materials are mixed to form the adhesive material. After the adhesive material has formed, the device 10 is used in the dispensing mode, in which the adhesive material is dispensed to a target area.

For example, the adhesive material may be a two-part bone cement, such as glass ionomer cements, that can be used for surgical procedures and the target area can be a fractured bone into which the adhesive material is dispensed. For example, the fractured bone may be a fractured human vertebra and the bone cement may be injected into the vertebra during a vertebroplasty operation. In this case, the first ingredient that is stored in chamber 1a can be a powder and the second ingredient that is stored in chamber 1b can be a liquid. For instance, in one example, the powder can be an ionomeric glass and the liquid can be an aqueous polyacrylic acid. In another example, the powder can be an ionomeric glass and dehydrated polyacrylic acid and the liquid can be water. In another example, the powder can be dehydrated acid and the liquid can be water with dissolved ionomeric glass therein. Accordingly, one of the components, e.g. the acid, the glass or the aqueous media is kept separate until they are mixed in the device 10. Therefore, any two of these components can be supplied premixed but the third component is kept separate from those mixed two components. FIG. 2 shows the chambers 1a and 1b.

While the various embodiments described herein describe the first and second ingredient materials being mixed to form an adhesive material, it should be understood that in at least one alternative embodiment, the first and second ingredient materials can be selected such that when they are mixed they form a third material which is a different kind of material that is not an adhesive material where there third material can be used in other applications.

The device 10 generally comprises a main housing 12, a first container 14, a nozzle 16, a handle 18 and a handle lock 21. The handle 18 comprises a finger grip 20 with an aperture 20a and the main housing 12 comprises finger grips 24 and 26 with apertures 24a and 26a respectively. A user may use the finger grips 20, 24 and 26 to hold and use the device 10. The device 10 further comprises a mixer 28 with a mixing element 30 as well as a removable sealing element (i.e. cap) 32. The handle lock 21 can be referred to as a safety release.

The device 10 can be entirely made of plastic which is sterilizable. For example, the device 10 can be subjected to ultraviolet light or to gamma radiation to sterilize the plastic components of the device 10.

The nozzle 16 is disposed at a first end of the device 10 for dispensing the adhesive material from the device 10 after mixing. The nozzle 16 comprises internal grooves for receiving a portion of the sealing element 32. The nozzle 16 may be sized and shaped so that it is a standard medical fitting that can be attached to a needle, a cannula, a medical tubing or another standard medical fitting for dispensing the adhesive material. For example, in some embodiments, the nozzle 16 can be sized to fit with a 9 gauge needle, a 14 gauge needle or a 16 gauge needle.

The sealing element 32 is removably attachable to the nozzle 16. The sealing element 32 is disposed and engaged with the nozzle 16 when the device 10 is used for storing and mixing the ingredient materials and the sealing element 32 is removed when the adhesive material is dispensed from the device 10. The sealing element 32 comprises a gripping portion 33 that a user may hold when mounting or removing the sealing element 32 from the nozzle 16. The sealing element 32 further comprises an engagement portion with grooves 33g on an external surface thereof that engage corresponding threads on an interior surface of the nozzle 16. In other embodiments, the sealing element 32 may be a pin and the interior surface of the nozzle 16 can be adapted to receive the pin and make a friction fit with the pin. The sealing element 32 may further comprise a seal 33s that is resilient and compliant, such as an o-ring for example, to provide additional sealing for the nozzle 16.

The first container 14 is disposed at a distal end of the device 10. The nozzle 16 is coupled with a first end 14a of the first container 14. In this example, the nozzle 16 is an integral portion of the first container 14. A distal portion of the first container 14 has sidewalls that define a first chamber 1a that is adapted to act as a storage chamber for storing a first ingredient material during the storage mode. The chamber 1a of the first container 14 is also adapted to act as a mixing chamber to mix the first ingredient material with a second ingredient material to create the adhesive material during the mixing mode. The chamber 1a is in fluid communication with the nozzle 16 to allow the adhesive material to be dispensed from the device 10 during the dispensing mode.

The first container 14 is in the form of a cylinder in this example embodiment and can be referred to as a first cylinder or a forward cylinder. The first container 14 comprises a mid-portion with a flange 14b that flares outwards and has an internal circumferential groove 14g. The side walls of the first container 14 further extend past the flange 14b to provide a guide region 14c in a proximal portion of the first container 14 where the side walls have two guide channels 15c that are formed along a portion thereof in the guide region 14c. The guide region 14c ends with a second flange 14f. The diameter of the side walls of the first container 14 that form the first chamber 1a and the diameter of the side walls are the guide region 14c are the same or substantially similar.

The device 10 further comprises a second container 34 that is disposed within the first container 14 and moveable therein. The second container 34 comprises a second chamber 1b that acts as a storage chamber for the second ingredient material. The second container 34 comprises a first end 36 with an aperture 36a and a sealing member 36s disposed adjacent to the first end 36 and extending circumferentially around the second container 34. The aperture 36a is in fluid communication with the first container 14. The sealing member 36s is resilient and compliant and may be an o-ring.

The second container 34 further comprises a guide region 35 formed by sidewalls at a proximal portion thereof and protrusions 37t that are adjacent a second end of the second container 34. The protrusions 37t are on the exterior of the walls of the second container 34 and are sized to slidingly engage the guide channels 15c of the first container 14. In this example embodiment, the protrusions 37t are formed by posts. The protrusions 37t have a height that is larger than the thickness of the side walls of the guide region 15c of the first container 14 so that the protrusions 37t can extend past the sidewalls of the first container 14 during use.

The second container 34 is in the form of a cylinder and may be referred to as a middle container. The sidewalls of a distal portion of the second container 34 define the second chamber 1b. The exterior side walls of the second container 34 are sized to be slightly narrower than the side walls of the guide region 14c of the first container 14 (i.e. the diameter of the second container 34 is smaller than diameter of the first container 14). This allows the second container 34 to slide within the guide region 14c of the first container 14 and be moveable with respect to the first container 14. The second container 34 is moveable within the first container 14 between a storage position in which the second ingredient material is stored in the chamber 1b of the second container 34 and a mixing position in which the second ingredient material is moved through the aperture 36a into the first container 14. The first chamber 1a extends from the inner surface of the distal end 14a of the first container 14 to the exterior of the end 36 of the second container 34.

In this example embodiment, the length of the second container 34 is smaller than the length of the guide region 14c of the first container 14, which allows the second container 34 to be fully contained within the first container 14 during the storing, mixing and dispensing modes as is shown in FIGS. 3-6, for example. In alternative embodiments, the length of the second container 34 may be larger or the same size as the length of the guide region 14c of the first container 14 to increase or decrease, respectively, the size of the mixing chamber during the mixing mode.

The sealing member 36s engages the internal surfaces of the side walls of the first container 14 for providing sealing for the first chamber 1a so that the first and second ingredients, during the mixing mode, or the adhesive material, during the dispensing mode do not leak from the mixing chamber past the second container 34 during use. This stops air (oxygen) and water from entering/exiting the chamber 1a (which may degrade the ingredients) and prevents the two ingredients from mixing prematurely.

In this example embodiment, the first and second containers 14 and 34 are made of transparent material which allows for visual inspection of the first and second ingredient materials during the storage and mixing modes. For example, the user can observe the purity and quality of the two ingredients prior to mixing and during mixing as well as observe the consistency of the adhesive material which will help in determining if the ingredient materials have been mixed together sufficiently. That being said, in other embodiments, the materials used to make the first and second containers 14 and 34 may not be transparent.

The mixer 28 longitudinally extends into the first and second containers 14 and 34 and is used to mix the first and second ingredient materials. The mixer 28 comprises a shaft (i.e. rod) having a first distal portion 28a and a second proximal portion 28b. The mixer 28 further comprises a mixing element 30 disposed at an end of the distal portion 28a, mixing grooves 29a (i.e. mixing slots) on an exterior surface of the distal portion of the mixer 28 but closer to the midpoint of the mixer 28. The mixer 28 further comprises a seal 27 at a mid-portion thereof and an engagement portion 29b at a proximal end of the proximal portion 28b of the mixer 28. The seal 27 is resilient and compliant and may be a sealing ring such as an o-ring, for example. The seal 27 provides a seal between the mixer 28 and the aperture 36a during the dispensing mode.

The mixing element 30 is disposed within the mixing chamber 1a of the first container 14 for mixing the first and second ingredient materials. The mixing element 30 is rotatable (see arrows 6r in FIG. 5) and longitudinally translatable within the mixing chamber 1a for mixing the first and second ingredient materials. Accordingly, the shaft of the mixer 28 is sized to slidingly move through the aperture 36a of the second container 36. The mixing element 30 is larger than the aperture 36a and the nozzle 16 such that its motion is constrained within the chamber 1a.

Figure 5:
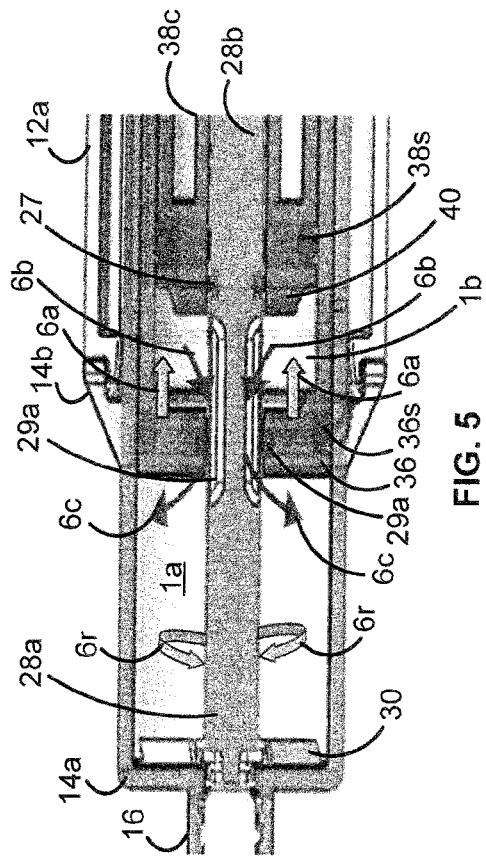
FIG. 5 is an enlarged top cross-sectional view showing movement of certain components of the device of FIG. 1 and the ingredient materials in an initial mixing configuration.

The mixing grooves 29a allow for the second ingredient material to move through the aperture 36a from the second container 34 to the first container 14 during the mixing mode as is shown by arrows 6b and 6c in FIG. 5. This is because during an initial portion of the mixing mode, a first portion of the mixing grooves 29a are disposed within the first container 14 and a second portion of the mixing grooves 29b are disposed within the second container 34 as shown in FIG. 5 to allow the second ingredient material to move from the second container 34 to the first container 14.

In this example embodiment, there are two mixing grooves 29a that are in the shape of rectangular slots that are on opposite portions of the surface of the mixer 28. In alternative embodiments, there may be more or less mixing grooves and they may have different shapes compared to one another and/or shapes that are different than a rectangular shape.

The engagement portion 29b of the mixer 28 engages a portion of the handle 18. This allows a user to control the mixer 28 by moving the handle 18. In this example embodiment, the engagement portion 29b comprises two slots in the distal portion 28b of the mixer 28 that form a neck portion and a club or head adjacent to the slots.

The device 10 further comprises a third cylinder 38 that may be referred to as a rear cylinder. The cylinder 38 is moveable with respect to the second container 34. Accordingly, the rear cylinder 38 has a diameter that is smaller than that of the second container 34. The rear cylinder 38 comprises an aperture 40a at a distal end 40, an axial channel 38c, a sealing member 38s, protrusions 41t and a proximal end 39 with an aperture 39a.

Figure 6:
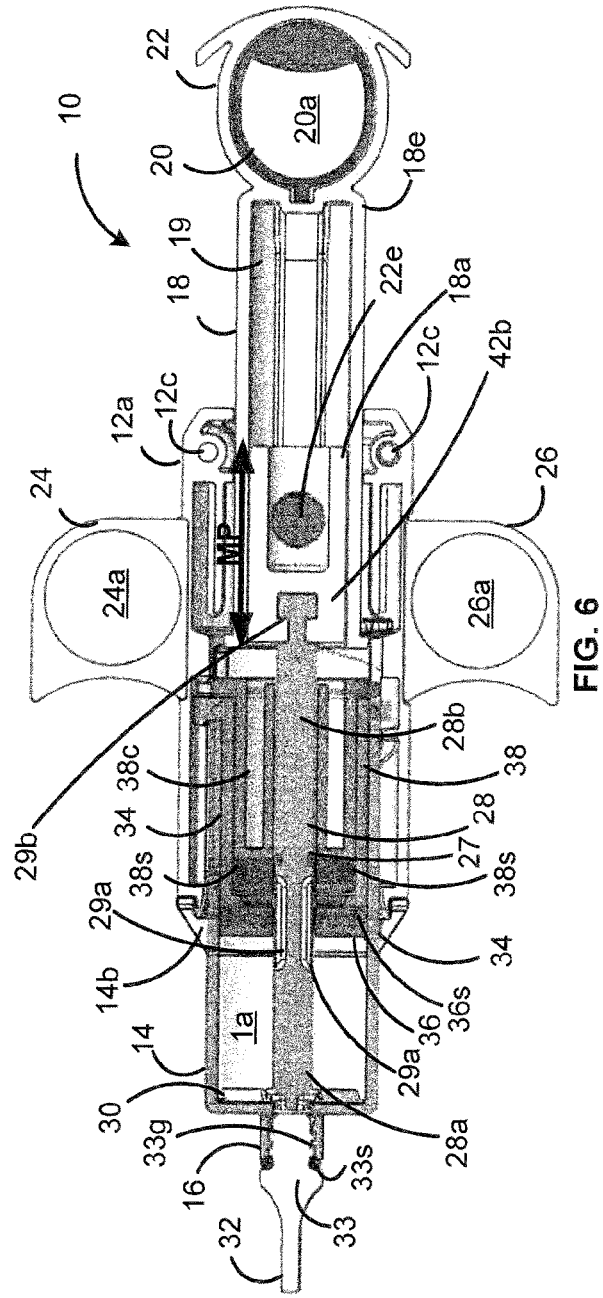
FIG. 6 is a top cross-sectional view of the device of FIG. 1 in a further mixing configuration.

The rear cylinder 38 is moveable between a storage position (see FIG. 3) and a mixing position (see FIG. 6). In the storage position, the second ingredient is stored in the second chamber 1b of the second container 34 and a distal portion of the rear cylinder 38 is received within the guide region 35 of the middle cylinder thereby defining the size of the second chamber 1b. The second chamber 1b extends from the inner surface of the distal end 36 of the second container 34 to the exterior of the end 40 of the rear cylinder 38. In the mixing position, the rear cylinder 38 is moved further into the second container 34 to provide a force that moves the second ingredient through the aperture 36a into the first container 14. In at least some embodiments, in the mixing position, the rear cylinder 38 is nested within the second container 34 and the second container 34 is nested within the first container 14 since all three cylinders 14, 34 and 38 are concentric and have progressively smaller diameters when moving from the distal end to the proximal end of the device 10.

The sealing member 38s is disposed around a circumference of the sidewalls of a distal portion of the cylinder 38 adjacent to the end 40. The sealing member 38s engages the internal surfaces of the side walls of the second container 34 for providing sealing for the second chamber 1b so that the second ingredient, during the storage or mixing modes, does not leak from the second chamber 1b past the rear cylinder 38 during use. The second sealing member 38s is resilient and compliant and may also be an o-ring. The sealing member 38s stops air (oxygen) and water from entering/exiting the chamber 1b (which may degrade the ingredients) and prevents the two ingredients from mixing prematurely.

The axial channel 38c runs along the length of the rear cylinder 38 between the ends 39 and 40 and is aligned with the aperture 40a. The diameter of the axial channel 38c is large enough to receive the shaft 28b of the mixer 28. The proximal portion of the mixer 28 is disposed within the axial channel 38c such that the engagement portion 29b of the mixer 28 extends past the aperture 39a to engage a portion of the handle 18 and the distal portion 28a of the mixer 28 extends past the aperture 40a.

The protrusions 41t are disposed on an exterior surface of the rear cylinder 38 adjacent to the proximal end 39 of the rear cylinder 38. The protrusions 41t are posts that are similar to the protrusions 37t of the container 34 and are sized to slidingly engage the guide channels 15c of the first container 14 in the same way as protrusions 37t.

Figure 7A:
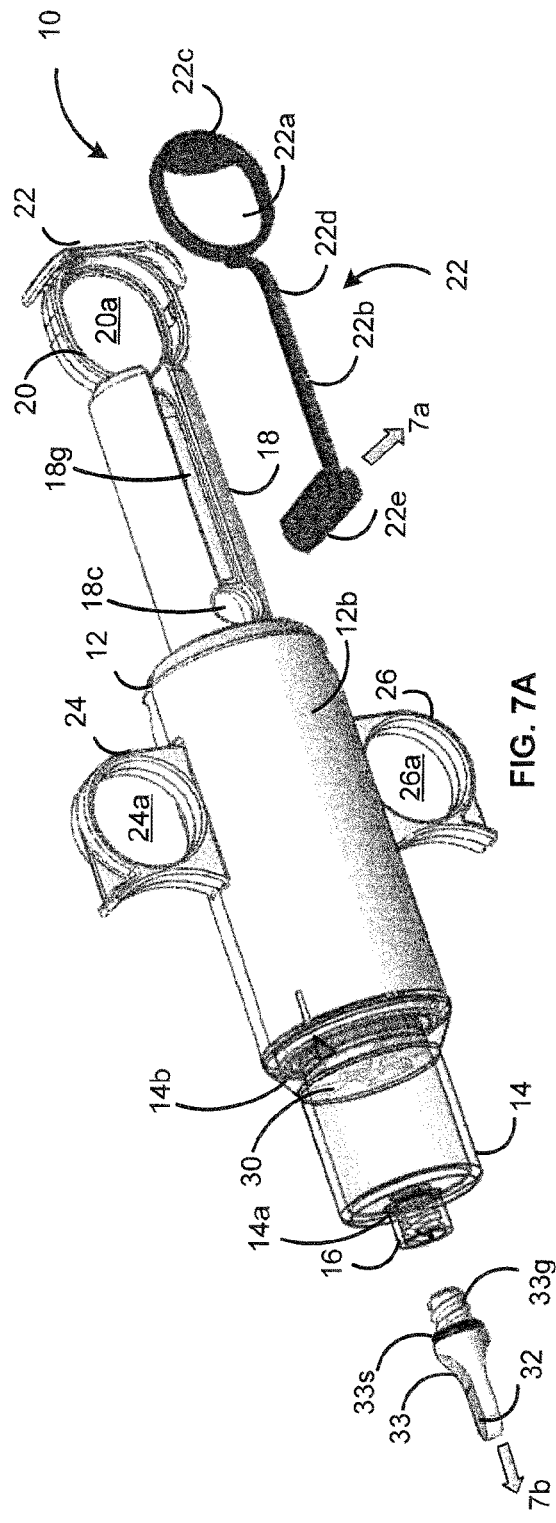
FIGS. 7A-7B are perspective and side cross-sectional views, respectively, of the device of FIG. 1 in a first dispensing configuration in which the injection lock and closure member are removed.
Figure 7B:
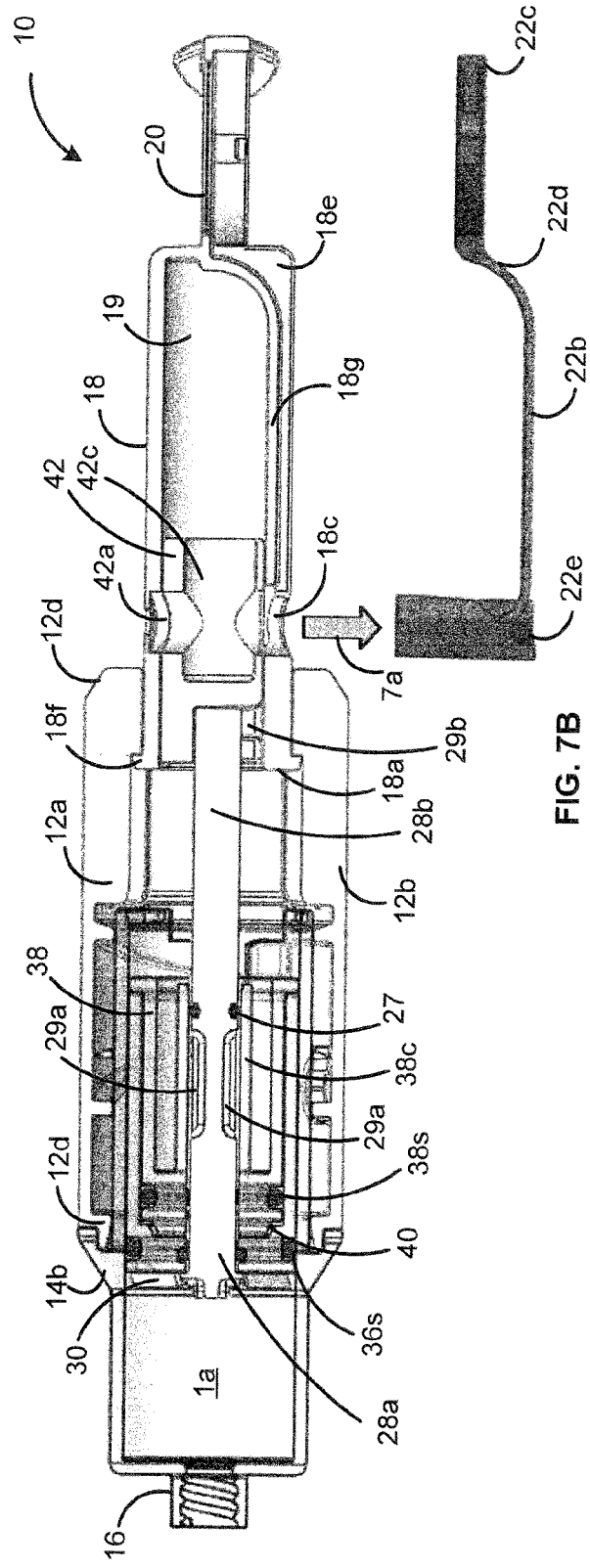
Figure 7C:
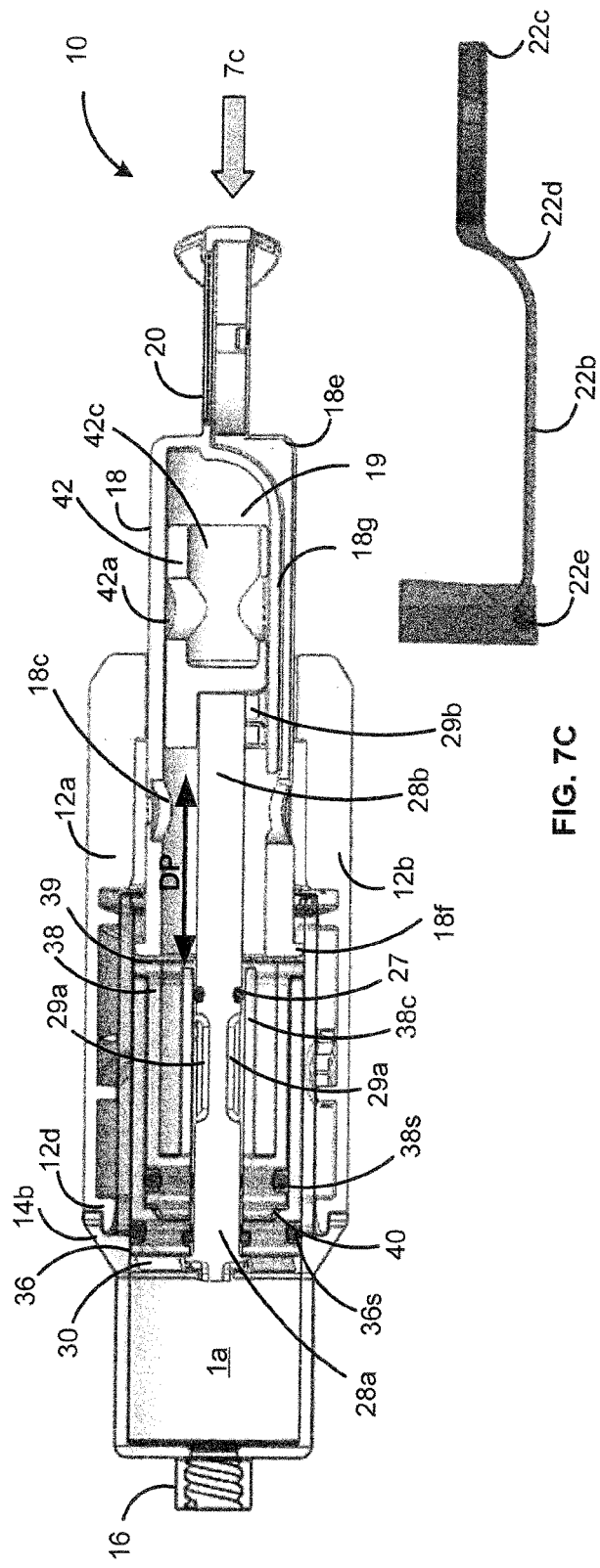
FIG. 7C is a side cross-sectional view of the device of FIG. 1 in a second dispensing configuration in which the plunger is initially depressed to start dispensing the mixed materials.

The proximal end 39 of the rear cylinder 38 has a flat annulus that defines the aperture 39a and provides a surface for receiving a distal portion of the handle 18 when a male locking member 22 of the handle lock 21 is removed (see FIGS. 7B-7C) which allows the handle 18 to move the rear cylinder 38 towards the first and second containers 14 and 34. A portion of the handle 18 engages (i.e. pushes against) the end 39 of the rear cylinder 38 during the mixing and dispensing modes when the male locking member 22 is removed.

In this example embodiment, the length of the rear cylinder 38 is the slightly smaller than the length of the second container 34 which allows the rear cylinder 38 to be fully contained within the second container 34 during the mixing and dispensing modes. Accordingly, the protrusions 41t abut against the protrusions 37t of the second container 34 when the rear cylinder 38 slides as far as possible within the second container 34. In alternative embodiments, the length of the rear cylinder 34 may be larger or smaller than the length of the second container 34 to increase or decrease, respectively, the size of the second chamber 1b during the storage mode.

The handle 18 is located at a proximal end of the device 10. The handle 18 is coupled to the mixer 28 to mix the first and second ingredient materials. The handle 18 is also coupled to the rear cylinder 38 which is used to move the second container 34 to a dispensing position to dispense the mixed adhesive material. The handle 18 comprises a hollow shaft with an axial channel 19 that extends longitudinally along at least a portion of the handle 18 to a distal end 18a having a flange 18f. In some embodiments, the axial channel 19 can also extend to a proximal end 18e of the handle 18 that is adjacent to the finger grip 20. The finger grip 20 comprises a ring with an aperture 20a. The handle 18 further comprises a groove 18g that extends along an exterior surface of the handle 18 to the proximal end 18e. A distal end of the groove 18g ends in an aperture 18c that opens into and is connected with the axial channel 19. The groove 18g and the aperture 18c are adapted to receive the male locking member 22 of the handle lock 21. In some embodiments, small ribs may be used in the groove 18g and/or in the ring 20 to retain the male locking member 22 in place. In some embodiments, the male locking member 22 may be a tear-off or break-away component, so that it cannot be reattached or reset after it is removed.

The removable handle lock 21 is disposed at the handle 18 and extends along a portion of the surface of the handle 18. The handle lock 21 comprises a male locking member 22 and a female locking member 42. When the handle lock 21 is in place the male locking member 22 engages the female locking member 42, and movement of the handle 18 is allowed along a mixing pathway MP (see FIG. 6) to move the mixer 28 to mix the first and second ingredient materials. When the handle lock 22 is removed and the male locking member 22 is disengaged from the female locking member 42, movement of the handle 18 is allowed along a dispensing pathway DP (see FIG. 7C) to move the second container 34 to the dispensing position in which the second container 34 is moved further into the first container 14 for dispensing the adhesive material through the nozzle 16 when it is ready to be dispensed.

The male locking member 22 is removably disposed along the groove 18g of the surface of the handle 18. The male locking member 22 comprises a shaft 22b with a handle 22c at the proximal end of the shaft 22b and a post 22e at the distal end of the shaft 22b. The handle 22c is a finger grip with an aperture 22a. The finger grip is a ring. In some alternative embodiments, the finger grip may have another shape. The handle 22c is disposed within the finger grip 20 of the device 10. The post 22e is sized to be slidingly received by the aperture 18c on the handle 18 and to be slidingly received by an aperture 42a on the female locking member 42. The post 22e engages the aperture 18c of the handle 18 and the aperture 42a of the female locking member 42 to constrain the movement of the handle 18 along the mixing pathway. The handle 22c is used by the user to remove the male locking member 22 from the groove 18g and the aperture 18c on the handle 18.

The female locking member 42 is shaped and sized to be received within the interior axial channel 19 at the distal portion of the handle 18. The female locking member 42 comprises the aperture 42a near a proximal end thereof that aligns with the aperture 18c of the handle 18 for coupling with the male locking member 22. The female locking member 42 further comprises an engagement portion 42b at a distal end for coupling with the engagement portion 29b of the mixer 28. The engagement portion 42b comprises a slot that is shaped to receive the engagement portion 29b of the mixer 28. In this example embodiment, the engagement portion 29b of the mixer 28 has a T-shape and the engagement portion 42b of the female locking member 42 is a similarly sized T-shaped slot. Once the mixer 28 is coupled to the female locking member 42 it is not removable unless the housing 12 of the device 10 is dismantled.

When the female locking member 42 is engaged with the mixer 28, the distal end of the female locking member 42 abuts against the face 39 of the rear cylinder 38 which allows the user to move the handle 18 and thereby move the rear cylinder 38 between its different operating positions as explained previously. The amount of distance that the user can move the rear cylinder 38 depends on whether the male locking member 22 is engaged with the female locking member 42 (i.e. the post 22e of the male locking member 22 is slid within the aperture 42a of the female locking member 42).

When the male locking member 22 is engaged with the female locking member 42, the proximal end of the female locking member 42 is fixed in position and does not extend distally past the distal end 18a of the handle 18 as is shown in FIG. 3. Since the engagement portion 29b of the mixer 28 is engaged with the engagement portion 42b of the female locking member 42, the mixer 28 is fixed to the female locking member 42 and in turn fixed to the handle 18. When the handle 18 is pushed towards the distal end of the device 10, the motion of the handle 18 is stopped by the mixing element 30 abutting against the distal end 14a of the first container 14 as is shown in FIG. 3.

Figure 7D:
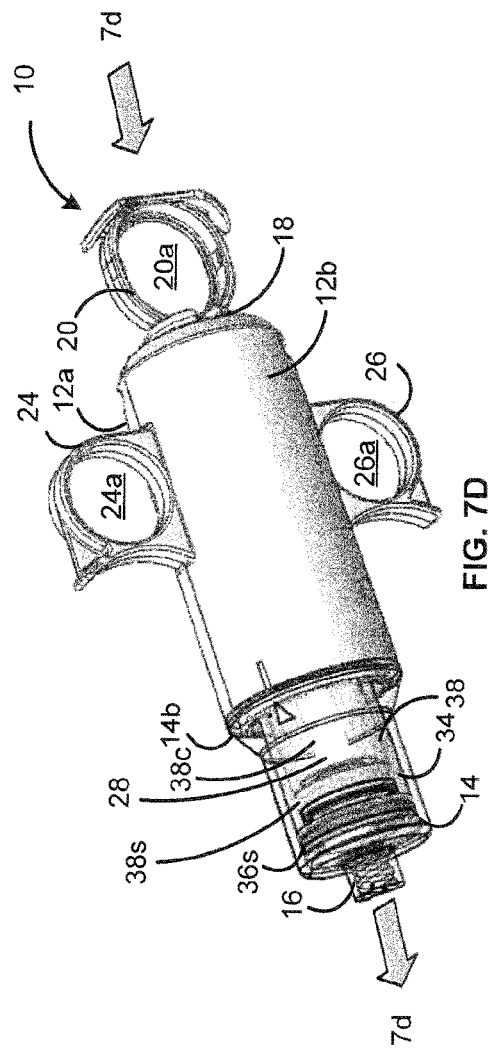
FIG. 7D is a perspective view of the device of FIG. 1 in a third dispensing configuration in which the plunger is fully depressed at the end of the dispensing process.

When the male locking member 22 is removed, the female locking member 42 is free to move within the handle 18 which allows the handle 18 to move axially independently of the mixer 28. The flange 18f at the distal end 18a of the handle 18 can therefore directly engage the face 39 of the rear cylinder 38 when the user moves the handle 18 towards the housing 12. The handle 18 is not constrained by the mixing element 30 abutting against the distal end 14a of the first container 14 since the female locking member 42 moves proximally inside the axial channel 19 of the handle 18 (see FIGS. 7C and 7D). Therefore, the handle 18 is allowed to move along the dispensing pathway DP (see FIG. 7C) where the distal portion of the handle 18 pushes the rear cylinder 38 and the second container 34 further into the first container 14 which applies pressure to the mixed adhesive material so that the user can dispense the mixed adhesive material from the device 10 as required. Since the distal portion 18a of the handle 18 only presses on the rear and middle cylinders 38 and 34, and does not connect with them, the user cannot draw the mixed adhesive material back into the device 10, which is beneficial since being able to draw the mixed adhesive material back into the device 10 is undesirable. The user can only apply positive pressure to the mixed adhesive material.

The housing 12 is disposed at a mid-portion of the device 10 with a portion of the first container 14 extending past a distal end 12d of the housing 12 and a portion of the handle 18 extending past the proximal end 12e of the housing 12. The distal end 12d comprises a neck portion that is adapted to engage the internal circumferential groove 14g of the flange 14b of the first container 12. The proximal end 12e has a truncated conical shape with a sloping edge that slopes towards the handle 18.

The housing 12 comprises two curved portions 12a and 12b that together form a cylindrical body for the device 10. The housing portions 12a and 12b comprise apertures 12c for receiving fasteners for attaching the housing portions 12a and 12b to one another. In one embodiment, the fasteners can be screws so that the housing portions 12a and 12b can be removably secured to one another. Alternatively, in some embodiments, the fasteners can be pins or bolts that are not removable so that the housing 12 cannot be taken apart after the device 10 is constructed.

The housing 12 further comprises first and second finger grips 24 and 26 that are disposed opposite one another on different sides of an exterior surface of the housing portions 12a and 12b. The finger grips 24 and 26 are rings that have apertures 24a and 26a, respectively. The handle 18 further provides the third finger grip 20. The finger grips 24 and 26 are sized to receive the forefinger and middle finger of a user while the finger grip 20 is sized to receive the user's thumb. This allows the user to hold the device 10 with one hand and provide an increased force when moving the handle 18 towards the housing 12 as the user is using both of their fingers to apply a pulling force and their thumb to apply a pushing force and both of these forces together result in a larger contractive force. The ability of a user to easily provide an increased amount of force when using the finger grips 20, 24 and 26 of the device 10 is advantageous when dispensing an adhesive material that is particularly dense and has a high viscosity.

Both the first container 14 and the second container 34 are rotatable with respect to the housing 12 for mixing the first and second ingredient materials. For example, when the device 10 is assembled, the neck 12d of the housing portions 12a and 12b is adjacent to and received in the circumferential groove 14g such that the first container 14 can rotate with respect to the housing 12.

Referring now to FIG. 4, the housing 12 comprises inclined grooves 12g on inner surfaces of the two housing portions 12a and 12b. The inclined grooves 12g may also be referred to as guide grooves or guide ramps. The inclined grooves 12g are engaged by the posts 37t of the second container 34 as well as the posts 41t of the rear cylinder 38. In particular, the posts 37t and the posts 41t radially extend past the sidewalls in the guide portion 14c of the first container 14 when the second container 34 and the rear cylinder 38 are disposed within the proximal portion of the first container 14 so that the posts 37t and 41t extend into and engage the inclined grooves 12g of the inner surface of the housing 12. Accordingly, the second container 34 and the rear cylinder 38 move axially with respect to the first container 14.

During use, when the first container 14 is twisted, via a twisting motion 4r, relative to the housing 12 this causes the posts 37t of the second container 24 to move along the inclined grooves 12g of the housing 12 which causes the second container 34 to rotate. At the same time the posts 37t are engaged within the linear guide channels 15c of the first container 14 which causes the second container 34 to move linearly away (see arrows 6a in FIG. 5) from the first container 14 such that the mixing grooves 29a are now disposed in both the first and second containers 14 and 34. At the same time the second container 34 moves closer to the rear cylinder 38 which reduces the size of the storage chamber 1b which causes the second ingredient material to then move (see arrows 6b and 6c in FIG. 5) along the mixing grooves 29a from the storage chamber 1b of the second container 34 into the chamber 1a of the first container 14. The chamber 1a now acts as a mixing chamber as is shown in FIGS. 5 and 6. The chamber 1a is now enlarged since the second container 34 has moved away from the first container 14.

The grooves 12g along the interior surface of the housing 12 comprise a hook-shaped stop portion 12s, which constrains the motion of the posts 37t thereby stopping the rotational and linear motion of the second container 34. The distance that the second container 34 moves away from the first container 14 is set by the shape, length and angle of the inclined grooves 12g and can be selected such that the size of the chamber 1a increases to be the size of the chamber 1b plus the original size of the chamber 1a (when it was used for storing the first ingredient during the storage mode) and the size of the second chamber 1b can become zero or minimal when the second container 34 stops moving. The interaction between the inclined grooves 12g and the protrusions 37t and 41t are such that the activation process (i.e. the mixing of the first and second ingredients) is irreversible and cannot be reset or stopped once initiated so the device 10 cannot accidentally be used twice.

It should be noted that the movement of the first and second containers 14 and 34 and the mixing of the first and second ingredients can be done while the device 10 is still locked and the handle lock 21 is still in place. When the adhesive material is prepared and is ready for use, the male portion of the handle lock 21 can then be removed so that the handle 18 can be further actuated to dispense the adhesive material from the nozzle 16 of the device 10.

The device 10 can be implemented such that the size of the first and second chambers 1a and 1b can be varied so that they hold sufficient amounts of ingredients that are needed to make an amount of adhesive material that is sufficient for the application for which the device 10 is used. For example, when the device 10 is used to hold reagents that are used to formulate a bone cement, the chamber sizes 1a and 1b, and therefore the amount of the reagents, can be implemented to be larger, such as 10 $cm^3$ for example, when a larger amount of bone cement is needed such as for knee or shoulder surgery, for example, whereas the chamber sizes 1a and 1b can be implemented to be smaller, such as 4 or 5 $cm^3$ for example, when a smaller amount of bone cement is needed such as for wrist surgery, for example.

In an example embodiment, the device 10 can be implemented such that it has an overall length of 210 mm, an overall height of 85.6 mm, and an overall width of 37.6 mm. Furthermore, the device 10 can be implemented so that the volume of chamber 1a during storage is 6.2 cc, the volume of chamber 1b during storage is 4.8 cc and the volume of chamber 1a when it is enlarged and used for mixing is 11 cc.

Referring now to FIG. 8A, illustrated therein is a flowchart of an example embodiment of a method 100 for making the device 10 for storing first and second ingredient materials, mixing the ingredient materials to form an adhesive material and dispensing the adhesive material in accordance with the teachings herein.

At act 102, the method 100 comprises inserting the first ingredient material into a first chamber 1a of a first container 14 having a nozzle 16 at a distal end and an open proximal end, the nozzle 16 being sealed by a removable sealing member 32.

At act 104, the method 100 comprises inserting a mixer 28 having a mixing element 30 on a distal end thereof longitudinally through an aperture on a distal end of a second container 34 having a second chamber 1b and an open proximal end;

At act 106, the method 100 comprises inserting a distal end 36 of the second container 34 into the first container 14 with the mixing element 30 on the distal end 28a of the mixer 28 extending into the first chamber 1a. The first and second containers 14 and 34 have a linear translational coupling that allows the second container 34 to move relative to the first container 14 and the rear cylinder 38. The linear translation coupling comprises the guide channels 15c on the guide portion 14c of the first container 14 and the protrusions 37t on the outer surface of the proximal end portion of the second container 34.

At act 108, the method 100 comprises inserting the second ingredient material into the second chamber 1b of the second container 34.

At act 110, the method 100 comprises inserting a distal end of a rear cylinder 38 into the second container 34 where the rear cylinder 38 has an axial channel 38c. The rear cylinder 38 is inserted into the second container 34 until the proximal end of the mixer 28 extends past a proximal end of the rear cylinder 38. The rear cylinder 38 and the first container 14 have a linear translational coupling that allows the rear cylinder 38 to move relative to the first container 14. The linear translation coupling comprises the guide channels 15c on the guide portion 14c of the first container 14 and the protrusions 41t on the outer surface of the proximal end portion of the rear cylinder 38.

At act 112, the method 100 comprises coupling the handle 18 with the handle lock 21 to the proximal end of the mixer 28 and to a proximal portion of the rear cylinder 38 using two coupling steps. For example, a female locking member 42 of the handle lock 21 is releasably coupled with the engagement portion 29b of the mixer 28 by engaging the female locking member 42 with the male locking member 22. In addition, the flange 18f of the distal end 18a of the handle 18 makes contact with the proximal face (e.g. annulus 39) of the rear cylinder 38.

At act 114, the method 100 comprises mounting a housing 12 around a proximal portion of the first container 14 and a distal portion of the handle 18. The housing 12 and the first container 14 have a rotational coupling (via the flange 14b with the circumferential groove 14g and the neck 12d of the housing 12). The housing 12 and the second container 34 as well as the rear cylinder 38 have a rotational and linearly translational coupling due to the inclined grooves 12g (on inner surfaces of the housing 12) being slidingly engaged by the protrusions 37t on the second container 34 and the protrusions 41t on the rear cylinder 28.

It should be noted that after act 114, when the ingredients have been stored and the device 10 has been assembled, the device 10 can be put into a sterilized bag or pouch that may also be sealed. Therefore, the device can be pre-filled with the first and second ingredients, put into a sterilized bag and then stored for periods of up to about one year before use if the sealing components of the device 10 and the sterilized bag provide adequate sealing.

Referring now to FIG. 8B, shown therein is a flowchart of an example embodiment of a method 150 of using the device 10 for mixing first and second ingredients to form an adhesive material and dispensing the adhesive material, where the device 10 is defined according to any of the embodiments described in accordance with the teachings herein.

At act 152, the method 150 comprises the user rotating the first container 14 relative to the housing 14 of the device 10. When the user twists the first container 14 in this manner, this causes the protruding features 37t and 41t on the second container 34 and the rear cylinder 38, respectively, to interact with the inclined grooves 12g on the inner surfaces of the housing portions 12a and 12b (see FIG. 4) which moves the second container 34 towards the rear cylinder 38. As the second container 34 moves towards the rear cylinder 38, the sealing member 36s that separates the storage chambers 1a and 1b passes over one or more mixing grooves (i.e. slots) 29a in the mixer 28. The mixing grooves 29a allow the second material to by-pass the sealing member 36 and move from the second storage chamber 1b into the first storage chamber 1a (see FIG. 5). In the case of bone cement, in an example embodiment, a liquid component in the second chamber 1b moves from the second storage chamber 1b into the first storage chamber 1a so that the two reactive parts of the bone cement are introduced together.

It should be noted that in an alternative embodiment, there may be only one protrusion 37t on the second cylinder 34, only protrusion on the rear cylinder 38, only one guide groove 15g on the first cylinder 14 and only one inclined groove 12g on the inner surface of the housing 12.

In some embodiments, the device 10 may be in a sealed sterile storage pouch so prior to rotating the first container 14, the user removes the device 10 from the sterile storage pouch in preparation for use.

In some embodiments, prior to rotating the first container 14, the user may also move the mixer 28, which is connected to the handle 18, to agitate the first ingredient material that is in the first storage chamber 1a. For example, when the first ingredient material is the powder component of a bone cement, caking of the powder may have occurred during storage, and so some initial agitation of the powder before use may be done to improve the mixing of the powder with the liquid ingredient material.

At act 154, the method 150 comprises the user using the mixer 28 to sufficiently and thoroughly mix the first and second ingredient materials for forming the adhesive material. The mixing can be done by simply moving the mixer 28, by using the handle 18, backwards and forwards. In addition, the handle 18 may be rotated to rotate the mixer 28. The mixer 28 has a mixing element 30, which in this example is a cross-shaped element, on the end of the mixer 28 that passes through the two ingredient materials forcing them to mix together. This direct mixing action provides the user, through the handle 18 and the mixer 28, with tactile feedback to indicate the consistency of the mixed adhesive material. The transparent portion of the container 14 provides the user with visual feedback of the mixed adhesive material in the chamber 1a. The user can then use this tactile feedback and/or visual feedback to determine whether further mixing is required. For example, when the adhesive material is a bone cement, the adhesive material becomes stiffer when it is sufficiently mixed and it is useful to understand when this occurs.

At act 156, the method 150 comprises the user removing the male locking member 22 of the handle lock 21 by using a pulling force 7a. When the male locking member 22 is removed, the handle 18 is disconnected from the mixer 28 (see FIGS. 7A-7C). At this point, the handle 18 is now capable of moving the rear cylinder 38 into a further distal position.

At act 158, the method 150 comprises the user removing the removable sealing element 32 from the nozzle 16 of the device 10 by applying a removal force 7b which may be a pulling force or a rotating force depending on the implementation of the sealing element 32. The removal of the sealing element 32 (which in this example embodiment is a sealing cap) allows the adhesive material to exit from the chamber 1a (that was acting as a mixing chamber) and to exit from the device 10.

At act 160, the method 150 comprises the user applying forces 7c and 7d (see FIGS. 7C-7D) to move the handle 18 towards the housing 12 of the device 10 to dispense the adhesive material. It should be noted that another force can be applied in a direction opposite to force 7c when the user's forefinger and middle finger pull back on the finger grips 24 an 26. The user may apply force to eject the adhesive material from the device 10 and the user can determine how well mixed the adhesive is by observing how the adhesive material moves upon application of the ejection force.

The device 10 is not intended to be reused, so once a sufficient amount of the adhesive material has been dispensed no further interaction is required. When the adhesive material is bone cement, any unused or residual bone cement will quickly set and prevent reuse of the device 10. In some embodiments, the user may attach the nozzle 32 to a needle, a cannula, a medical tubing or another standard medical fitting prior to dispensing the adhesive material.

It should be noted that as soon as the two ingredient materials are mixed sufficiently to form the adhesive material the user may have a limited amount of time to dispense the adhesive material before it becomes no longer useable. For example, in the case of mixing the ingredient materials to form bone cement as the adhesive material, the bone cement has a limited lifetime before it becomes unworkable and sets solid. Advantageously, the device 10 is constructed so that it is quick and simple to dispense the adhesive material.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

The invention claimed is:

1. A device for storing ingredient materials, mixing the ingredient materials to form a third material and dispensing the third material, wherein the device comprises:
   a nozzle at a first end of the device for dispensing the third material from the device after mixing;
   a first container at a distal end of the device and coupled with the nozzle, the first container being adapted to store a first ingredient material and mix the first ingredient material with a second ingredient material to create the third material;
   a second container that is disposed within a distal portion of the first container, has an aperture in communication with the first container and is moveable within the device between a storage position in which a second ingredient material is stored in the second container and a mixing position in which the second ingredient material is moved to the first container;
   a mixer that longitudinally extends into the first and second containers and is used to mix the first and second ingredient materials;
   a handle at a proximal end of the device, the handle being coupled to the mixer to mix the first and second ingredient materials and the handle also being coupled to the second container to move the second container to a dispensing position to dispense the third material; and
   a removable sealing element disposed at the nozzle when storing and mixing the first and second ingredient materials and being removed when dispensing the third material from the device.

2. The device of claim 1, wherein the device further comprises a removable handle lock that is disposed at the handle, wherein when the handle lock is in place movement of the handle is allowed along a mixing pathway to move the mixer and when the handle lock is removed movement of the handle is allowed along a dispensing pathway to move the second container to the dispensing position in which the second container is moved further into the first container for dispensing the third material.

3. The device of claim 1, wherein the first and second containers are made of transparent material allowing for visual inspection of the first and second ingredient materials during storage and mixing.

4. The device of claim 1, wherein the device comprises a housing disposed at a mid-portion of the device with a portion of the first container extending past a distal end of the housing, a portion of the handle extending past a proximal end of the housing and both the first container and the second container being rotatable with respect to the housing for mixing the first and second ingredient materials.

5. The device of claim 4, wherein the housing comprises first and second finger grips disposed on opposite sides of an exterior surface of the housing and the handle comprises a third finger grip at a proximal end thereby allowing a user to hold the device and move the handle towards the housing during mixing and/or dispensing.

6. The device of claim 5, wherein the finger grips are rings.

7. The device of claim 4, wherein:
the first container comprises sidewalls with at least one guide channel along a portion of the sidewalls;
the housing comprises at least one inclined groove on an inner surface thereof; and
the second container comprises at least one protrusion on an outer surface thereof that is received within the at least one guide channel and radially extends past the sidewalls of the first container and extends into and engages the at least one inclined groove of the housing,
wherein during use the first container is twisted relative to the housing thereby causing the at least one protrusion of the second container to move along the at least one inclined groove of the housing and move the second container away from the distal end of the first container to move the second ingredient material from the second container to the first container.

8. The device of claim 7, wherein the first container comprises a first cylinder having:
the nozzle at a first end of the cylinder;
a first chamber formed by sidewalls of a distal portion of the first cylinder, the first chamber acting as a storage chamber and as a mixing chamber and being in fluid communication with the nozzle; and
a first guide region formed by sidewalls of a proximal portion of the first cylinder and the at least one guide channel is located in the first guide region.

9. The device of claim 8, wherein the second container comprises a second cylinder moveable with respect to the first cylinder and having a diameter smaller than a diameter of the first cylinder, the second cylinder having:
a first end having an aperture in communication with the first cylinder;
a second chamber formed by sidewalls of a distal portion of the second cylinder, the second chamber acting as a second storage chamber for the second ingredient material;
a first sealing member disposed around a portion of the distal sidewalls of the second chamber for providing sealing for the first chamber; and
a second guide region formed by sidewalls of a proximal portion of the second cylinder and the at least one protrusion is located on an outer surface of the second guide region,
wherein the second container is received within the first guide region.

10. The device of claim 9, wherein the device further comprises a rear cylinder moveable with respect to the second cylinder and having a diameter smaller than a diameter of the second cylinder, the rear cylinder comprising:
an aperture at a distal end;
an axial channel aligned with the aperture, the mixer extending along the axial channel through the aperture;
at least one protrusion on an exterior surface of the rear cylinder for sliding within the at least one guide channel of the first cylinder during use;
a flat surface at a proximal end of the rear cylinder for receiving a distal portion of the handle when the handle lock is removed thereby moving the rear cylinder towards the first and second cylinders; and a second sealing member disposed around the distal sidewalls of the rear cylinder for providing sealing for the second chamber.

11. The device of claim 1, wherein the mixer comprises at least one mixing groove on an outer surface thereof wherein during mixing a first portion of the at least one mixing groove is disposed within the first container and a second portion of the at least one mixing groove is disposed within the second container to allow the second ingredient material to move from the second container to the first container during mixing.

12. The device of claim 11, wherein the mixer comprises a mixing element at an end portion thereof which is disposed within the first container for mixing the first and second ingredient materials.

13. The device of claim 12, wherein the mixing element is rotatable and longitudinally translatable for mixing the first and second ingredient materials.

14. The device of claim 1, wherein
the handle comprises a groove on an exterior surface thereof, an aperture at one end of the groove and an interior axial channel at a distal end thereof coupled with the aperture; and
the handle lock comprises:
a female locking member that is sized to be received within the interior axial channel of the handle and has an aperture at a proximal end that aligns with the aperture of the handle and a distal end with an engagement member that is coupled with the mixer; and
a male locking member removably disposed within the groove on the handle and having a post at a distal end thereof for engaging the apertures of the handle and the female locking member to constrain the movement of the handle along the mixing pathway.

15. The device of claim 14, wherein the male locking member comprises a handle at a proximal end thereof for removing the male locking member from the groove on the handle.

16. The device of claim 15, wherein the handle of the male locking member is a finger grip ring that is disposed within the finger grip of the handle.

17. The device of claim 14, wherein when the male locking member is removed the female locking member is free to move within the handle allowing the handle to move along the dispensing pathway where a distal portion of the handle pushes the second container further into the first container to dispense the third material from the device.

18. The device of claim 1, wherein the third material is an adhesive material.

19. The device of claim 18, wherein the first ingredient material stored in the first chamber is a powder and the second ingredient material stored in the second chamber is a liquid, wherein the powder comprises an ionomeric glass and the liquid comprises an aqueous polyacrylic acid.

20. The device of claim 18, wherein the first ingredient material stored in the first chamber is a powder and the second ingredient material stored in the second chamber is a liquid, wherein the powder comprises an ionomeric glass and dehydrated polyacrylic acid and the liquid comprises water.

21. The device of claim 18, wherein the first ingredient material stored in the first chamber is a powder and the second ingredient material stored in the second chamber is a liquid, wherein the powder comprises dehydrated acid and the liquid comprises water having dissolved ionomeric glass therein.

22. A method of using a device for mixing first and second ingredients to form a third material and dispensing the third material, the device being defined according to claim 1, wherein the method comprises:
- rotating the first container relative to the housing of the device;
- using the mixer to mix the first and second ingredients for forming the third material;
- removing the male locking member of the handle lock;
- removing the removable sealing element from the nozzle; and
- moving the handle towards the housing of the device to dispense the third material.

23. A device for storing first and second ingredient materials, mixing the ingredient materials to form a third material and dispensing the third material, wherein the device comprises:
- a nozzle and having a removable sealing element;
- a housing;
- a first container rotatably coupled to the housing, being in fluid communication with the nozzle, and having a first chamber for storing the first ingredient material during storage;
- a second container disposed in the first container and in the housing, having a second chamber for storing the second ingredient material during storage and an aperture that is in fluid communication with the first container, the second container being linearly moveable with respect to the first container and rotatably coupled to the housing;
- a rear cylinder being disposed in the housing and in the first container proximal to the second container, the rear cylinder having a second aperture at a distal end, the rear cylinder being linearly moveable with respect to the first container and rotatably coupled to the housing;
- a mixer that longitudinally extends through the apertures of the second container and the rear cylinder into the first chamber for mixing the first and second ingredient materials during mixing; and
- a handle extending from a proximal end of the housing and having a handle lock, the handle being coupled to the mixer to control the mixer when the handle lock is in place and the handle being coupled to the rear cylinder to move the rear cylinder and the second container toward the nozzle to dispense the third material from the first container when the handle lock and the sealing element are removed, wherein, during use, when the first container is rotated the second container moves towards the rear cylinder, the second chamber reduces in size, the first chamber increases in size and the second material moves into the first chamber for mixing.

24. A method of making a device for storing first and second ingredient materials, mixing the ingredient materials to form a third material and dispensing the third material, wherein the method comprises:
- inserting the first ingredient material into a first chamber of a first container having a nozzle at a distal end and an open proximal end, the nozzle being sealed by a removable sealing member;
- inserting a mixer having a mixing element longitudinally through an aperture on a distal end of a second container having a second chamber and an open proximal end;
- inserting a distal end of the second container into the first container with the mixing element of the mixer extending into the first chamber, the first and second containers having a linear translational coupling;
- inserting the second ingredient material into the second chamber of the second container;
- inserting a rear cylinder having an axial channel into the second container with a proximal end of the mixer extending past a proximal end of the rear cylinder, the rear cylinder and the first container having a linear translational coupling;
- coupling a handle with a handle lock to the mixer; and
- mounting a housing around a proximal portion of the first container and a distal portion of the handle, the housing and the first container having a rotational coupling and the housing and the second container and the rear cylinder having a rotational and linear translational coupling.

25. The method of claim 24, wherein the third material is an adhesive material.

26. The method of claim 25, wherein the first ingredient material stored in the first chamber is a powder and the second ingredient material stored in the second chamber is a liquid, wherein the powder comprises an ionomeric glass and the liquid comprises an aqueous polyacrylic acid.

27. The method of claim 25, wherein the first ingredient material stored in the first chamber is a powder and the second ingredient material stored in the second chamber is a liquid, wherein the powder comprises an ionomeric glass and dehydrated polyacrylic acid and the liquid comprises water.

28. The method of claim 25, wherein the first ingredient material stored in the first chamber is a powder and the second ingredient material stored in the second chamber is a liquid, wherein the powder comprises dehydrated acid and the liquid comprises water having dissolved ionomeric glass therein.

* * * * *